United States Patent [19]

Hellstrand et al.

[11] Patent Number: 6,071,509

[45] Date of Patent: *Jun. 6, 2000

[54] ENHANCED ACTIVATION OF NATURAL KILLER CELLS USING AN NK CELL ACTIVATOR AND A HYDROGEN PEROXIDE SCAVENGER OR INHIBITOR

[75] Inventors: Jan Urban Kristoffer Hellstrand, Gothenburg; Svante Hermod Hermodsson, Molndal, both of Sweden

[73] Assignee: Maxim Pharmaceuticals, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/681,108

[22] Filed: Jul. 22, 1996

Related U.S. Application Data

[63] Continuation of application No. 08/287,200, Aug. 8, 1994, abandoned.

[51] Int. Cl.$^7$ ............................ A61K 45/00; A61K 38/21
[52] U.S. Cl. ...................... 424/85.2; 424/85.1; 424/85.4
[58] Field of Search ................................. 424/85.1, 85.2, 424/85.4

[56] References Cited

U.S. PATENT DOCUMENTS

| 4,690,915 | 9/1987 | Rosenberg ................................. 514/2 |
| 5,348,739 | 9/1994 | Hellstrand et al. .................... 424/85.2 |

FOREIGN PATENT DOCUMENTS

| 0 247 613 A2 | 12/1987 | European Pat. Off. . |
| 7-165582 | 6/1995 | Japan . |
| WO 93/24144 | 12/1993 | WIPO . |

OTHER PUBLICATIONS

"Remission maintenance therapy with histamine and interleukin–2 in acute myelogenous leukaemia" Brune, et al., *British Journal of Haematology*, 92:620–626, 1996.

"Hydrogen peroxide as a potent activator of T lymphocyte functions" Los, et al., *Eur. Journal of Immunology*, 25:159–165, 1995.

"Effect of Reactive Oxygen Intermediates and Antioxidants on Proliferation and Function of T Lymphocytes" Dröge, et al., *Methods in Enzymology*, 234:135–151, 1994.

"Antioxidants Inhibit Proliferation and Cell Surface Expression of Receptors for Interleukin–2 and Transferrin in T Lymphocytes Stimulated with Phorbol Myristate Acetate and Ionomycin" Chaudhri, et al., *Cellular Immunology*, 115:204–213, 1988.

"Hydroxyl radical scavengers inhibit lymphocyte mitogenesis" Novogrodsky, et al., *Proc. Natl. Acad. Sci. USA*, 79:1171–1174, Feb. 1982.

The Influence of Intraperitoneal Injections of Histamine on Tumor Growth in Fibrosarcoma–Bearing Mice. Burtin, et al., *Cancer Letters*, 12: 195–201, Jan. 1981.

Successful Tumor Immunotherapy with Cimetidine in Mice, Osband, et al., *The Lancet*, No. 8221, 1: 636–638, Mar. 21, 1981.

Suppression of Natural Killing in Vitro by Monocytes and Polymorphonuclear Leukocytes. Seaman, et al., *The Journal of Clinical Investigation*, 69: 876–888. Apr. 1982.

The Differential Effects of Human Leukocytic Pyrogen/ Lymphocyte–Activating Factor, T Cell Growth Factor, and Interferon on Human Natural Killer Activity, Dempsey, et al., *The Journal of Immunology*, May 17, 1982.

Tumor–Enhancing Effects of Cimetidine, Barna, et al., *Oncology*, 40: 43–45. 1983.

Combination of Cimetidine with other Drugs for Treatment of Cancer, Thornes, et al., *New England Journal of Medicine* 308: 591–592, Mar. 10, 1983.

The Influence of Histamine on Immune and Inflammatory Responses, Beer, et al., *Advances in Immunology*, 35: 209–268, 1984.

Hydroxyl radical scavengers inhibit human natural killer cell activity, Suthanthiran, et al., *Nature* 307: 276–278, Jan. 1984.

Enhancement by serotonin of intra–tumor penetration of spleen cells, Lespinatas, et al., *Br. J. Cancer*, 50: 545–547, Apr. 5, 1984.

Compared Mechanisms of Tumor Cytolysis by Human Natural Killer Cells and Activated Polymorphonuclear Leukocytes, Abrams, et al., *The Journal of Immunology* 132: No. 6, 3192–3196, Jun. 1984.

Down–Regulation of Human Natural Killer Activity Against Tumors by the Neutrophil Myeloperoxidase System and Hydrogen Peroxide, El–Hag, et al., *The Journal of Immunology* 133: No. 6, 3291–3297, Dec. 1984.

Effect of Ascorbic Acid on Human Natural Killer Cells, Huwyler, et al., *Immunology Letters*, 10: 173–176, 1985.

The Role of Natural Killer Cells in the Control of Tumor Growth and Metastasis, Nabil Hanna. *Biochimica et Biophysica Acta*. 780: 213–226, 1985.

Induction of Interferon–γ Production by Human Natural Killer Cells Stimulated by Hydrogen Peroxide, Munakata, et al., *The Journal of Immunology*, 134: No. 4, 2449–2455, Apr. 1985.

Natural Killer Cell–Mediated Lysis Involves an Hydroxyl Radical–Dependent Step, Duwe, et al., *The Journal of Immunology*, 134: No. 4, 2449–2455, Apr. 1985.

(List continued on next page.)

Primary Examiner—Bennett Celsa
Assistant Examiner—Maurie Garcia
Attorney, Agent, or Firm—Knobbe, Martens, Olson & Bear, LLP

[57] ABSTRACT

An improved method for the prevention of the inactivation of natural killer (NK) cells and the enhanced activation of NK cells in the presence of monocytes using a combination of a natural killer cell activator and a compound effective to inhibit the production or release of intracellular hydrogen peroxide, or a hydrogen peroxide scavenger, is disclosed. The method is useful, for example, in the treatment of solid tumors, metastases and viral infection.

16 Claims, 10 Drawing Sheets

OTHER PUBLICATIONS

Cytotoxicity by human adherent cells: oxygen–dependent and –independent cytotoxic reactions by different cell populations, Kessel, et al., *Immunology*, 58: 291–296, 1986.

Histamine augments interleukin–2 production and the activation of cytotoxic T lymphocytes, *Chemical Abstracts*. 104: No. 146898m, p. 146891.

Histamine Augments Interleukin–2 Production and the Activation of Cytotoxic T Lymphocytes, Dröge, et al., *Immunopharmacology*, 11: 1–6, 1986.

Histamine Inhibits Interferon–γ Production via Suppression of Interleukin 2 Synthesis, Dohlsten, et al., *Cellular Immunology*, 101: 493–501, 1986.

Histamine–Induced Suppressor Factor Inhibition of NK Cells: Reversal with Interferon and Interleukin 2, Nair, et al., *The Journal of Immunology*, 136: No. 7, 2456–2462, Apr. 1, 1986.

Hydeoperoxide Metabolism in Cyanobacteria, Tel–Or. et al., *Archives of Biochemistry and Biophysics*, 246: No. 1, 396–402, Apr. 1986.

Histamine $H_2$–Receptor–Mediated Regulation of Human Natural Killer Cell Activity, Hellstrand, et al., *The Journal of Immunology*, 137: No. 2, Jul. 15, 1986.

Biogenic Amines in the Regulation of Human Natural Killer Cell Cytotoxicity, Hellstrand, 1987.

Differential Effects of Histamine Receptor Antagonists on Human Natural Killer Cell Activity, Hellstrand, et al., *Int. Archs Allergy appl. Immunology*, 84: 247–255, 1987.

Selective, Histamine–Mediated Immunosuppression in Laryngeal Cancer, Richtsmeier, et al., *Ann Otol Rhinol Laryngol*, 96: No. 5, 569–572, 1987.

Clinical Improvement in Advanced Cancer Disease After Treatment Combining Histamine and H2–Antihistaminics (Ranitidine or Cimetidine), Burtin, et al., Accepted Jun. 1987.

Role of Serotonin in the Regulation of Human Natural Killer Cell Cytotoxicity, Hellstrand, et al., *The Journal of Immunology*, 139: No. 3, Aug. 1, 1987.

The IL–2 Receptor β Chain (p70): Role in Mediating Signals for LAK, NK, and Proliferative Activities, Siegel, et al., *Science*, vol. 238, Oct. 2, 1987.

Chondrocyte Antioxidant Defenses: The Roles of Catalase and Glutathione Peroxidase in Protection Against $H_2O_2$ Dependent Inhibition of Proteoglycan Biosynthesis, Baker, et al., *The Journal of Rheumatology*, 15: No. 4, 670–677, 1988.

Role of Flavonoids in the Oxygen–Free Radical Modulation of the Immune Response, Pignol, et al., *Plant Flavonoids in Biology & Medicine II: Biochemical, Cellular . . .* 173–182, 1988.

Flavone–8–Acetic Acid Augments Systemic Natural Killer Cell Activity and Synergizes with IL–2 for Treatment of Murine Renal Cancer, Wiltrout, et al., *The Journal of Immunology*, 140: No. 9, 3261–3265, May 1, 1988.

Interleukin–2: Inception, Impact, and Implications, Kendall A. Smith, *Science*, 240: 1169–1176, May 27, 1988.

Enhancement of Natural Killer Activity in Human Peripheral Blood by Flavone Acetic Acid, Urba, et al., *The Journal of the National Cancer Institute*, 80: No. 7, 521–525, Jun. 1, 1988.

The Development of New Immunotherapies for the Treatment of Cancer Using Interleukin–2, Rosenberg, *Annals of Surgery*, 208: No. 2, 121–135, Aug. 1988.

Interleukin 2 as a Pharmacologic Reagent, Lotze, et al., Chapter 12 from the National Institutes of Health, Oct. 28, 1988.

Augmentation of Natural Killer Activity, Induction of IFN and Development Tumor Immunity During the Successful Treatment of Established Murine Renal Cancer Using Flavone Acetic Acid and IL–2, Hornung, et al., *The Journal of Immunology*, 141: No. 10, 3671–3679, Nov. 15, 1988.

Enhancement of Human Natural Killer Cell Function by the Combined Effects of Tumor Necrosis Factor α or Interleukin–1 and Interferon–α or Interleukin–2, Østensen, et al., *Journal of Biological Response Modifiers*, 8: 53–61, 1989.

Suppression of human natural killer cell cytotoxicity by interleukin–2, Hellstrand, et al., *Clin. Exp. Immunol.* 77: 410–416, 1989.

Comparative Effect of Recombinant Il–1, –2, –3, –4, and –6, IFN–γ, Granulocyte–Macrophage–Colony–Stimulating Factor, Tumor Necrosis Factor–α, and Histamine–Releasing Factors on the Secretion of Histamine From Basophils, Alam, et al., *The Journal of Immunology*, 142: No. 10, 3431–3435, May 18, 1989.

Activation of Natural Killer Cells via the p75 Interleukin 2 Receptor, Phillips, et al., *J. Exp. Med.*, 170: 291–296, Jul. 1989.

Inhibition of Lymphokine–Activated Killer–and Natural Killer–Mediated Cytotoxicities by Neutrophils, Shau, et al., *The Journal of Immunology*, 143: No. 3, 1066–1072, Aug. 1989.

Regulation of Human Basophil Mediator Release by Cytokines, Schleimer, et al., *The Journal of Immunology*, 143: No. 4, 1310–1317, Aug. 15, 1989.

Inhibition of Lymphokine–activated Killer Cell Function by Human Alveolar Macrophages, Roth, et al., *Cancer Research*, 49: 4690–4695, Sep. 1989.

A Cell–to–Cell Mediated Interaction Involving Monocytes and Non T/CD16* Natural Killer (NK) Cells is Required for Histamine $H_2$–Receptor–Mediated NK–Cell Activation, Hellstrand, et al., *Scand J. Immunol.* 31: 631–644, 1990.

Deficiency in Catalase Activity Correlates with the Appearance of Tumor Phenotype in Human Keratinocytes, Rabilloud, et al., *Int. J. Cancer*, 45: 952–956, 1990.

Enhancement of Human Natural Killer Cell Cytotoxicity by Serotonin: Role of Non–T/CD16* NK Cells, Accessory Monocytes, and 5–$HT_{1A}$ Receptors, Hellstrand, et al., *Cellular Immunology*, 127: 199–214, 1990.

Flavone acetic acid antitumour activity against a mouse pancreatic adenocarcinoma is mediated by natural killer cells, Damia, et al., *Cancer Immunol Immunother.* 32: 241–244, 1990.

Monocyte–Mediated Suppression of IL–2–Induced NK–Cell Activation, Hellstrand, et al., *Scand J. Immunol.* 32: 183–192, 1990.

Possible involvement of adenosine 3':5'–cyclic monophosphate and extracellular calcium ions in histamine stimulation of interleukin–1 release from macrophage–like P38801 cells.

Okamoto, et al., *Immunology*, 70: 186–190, 1990.

Synergistic Activation of Human Natural Killer Cell Cytotoxicity by Histamine and Interleukin–2, Hellstrand, et al., *Int. Arch. Allergy Appl. Immunology*, 92: 379–389, 1990.

Histamine Type 2–Receptor Antagonists and Cancer Immunotherapy, Tom Smith, MD, *Comprehensive Therapy*, 16: No. 1, 8–13, 1990.

Splenic Versus Hepatic Artery Infusion of Interleukin–2 in Patients with Liver Metastases, Mavligit, et al., *Journal of Clinical Oncology*, 8: No. 2, 319–324, 1990.

Renal Cell Carcinoma: Treatment with Recombinant Interleukin–2 Plus Beta–Interferon, Krigel, et al., *Journal of Clinical Oncology*, 8: No. 3, 460–467, Mar. 1990.

High–Dose Recombinant Interleukin–2 Alone: A Regimen With Limited Activity in the Treatment of Advanced Renal Cell–Carcinoma, Abrams, et al., *Journal of the National Cancer Institute*, 82: No. 14, 1202–1206, Jul. 18, 1990.

Recombinant Interleukin–2 and Adoptive Immunotherapy Alternated with Decarbazine Therapy in Melanoma: A National Biotherapy Study Group Trial, Dilman, et al., *Journal of the National Cancer Institute*, 82: No. 16, 1345–1348, Aug. 15, 1990.

Immunological Effects of Flavone Acetic Acid, Trizzi, et al., *Cancer Research*, 50: 6483–6485, Oct. 15, 1990.

Role of Histamine in Natural Killer Cell–Mediated Resistance Against Tumor Cells, Hellstrand, et al., *The Journal of Immunology*, 145: No. 12, Dec. 15, 1990.

Cell–to–Cell Mediated Inhibition of Natural Killer Cell Proliferation by Monocytes and its Regulation by Histamine $H_2$–Receptors, Hellstrand, et al., *Scand J. Immunol.* 34: 741–752, 1991.

Induction of Natural Killer Activity by Xanthenone Analogues of Flavone Acetic Acid: Relation with Antitumour Activity, Ching, et al., *Eur. J. Cancer*, 27: No. 1, 79–83, 1991.

In vitro Methods for Screening Agents with an Indirect Mechanism of Antitumour Activity: Xanthenone Analogues of Flavone Acetic Acid, Ching, et al., *Eur. J. Cancer*, 27: No. 12, 1684–1689, 1991.

Monocyte–Induced Down–Modulation of CD16 and CD56 Antigens on Human Natural Killer Cells and its Regulation by Histamine $H_2$–Receptors, Hellstrand, et al., *Cellular Immunology*, 138: 44–45, 1991.

Natural killer (NK) and lymphokine activated killer (LAK) cell activity in patients (PTS) treated with Flavone acetic acid (FAA), Galligioni, *Annals of Oncology*, 2: 145–150, 1991.

Production of Large Amounts of Hydrogen Peroxide by Human Tumor Cells, Szatrowski, et al., *Cancer Research*, 51: 794–798, Feb. 1991.

A Phase II Study of High–Dose Continuous Infusion Interleukin–2 With Lymphokine–Activated Killer Cells in Patients With Metastatic Melanoma, Dutcher, et al., *Journal of Clinical Oncology*, 9: No. 4, 641–648, Apr. 1991.

Continuous Interleukin–2 and Lymphokine–Activated Killer Cells for Advanced Cancer: A National Biotherapy Study Group Trial, Dilman, et al., *Journal of Clinical Oncology*, 9: No. 7, 1233–1240, Jul. 1991.

Sequential Administration of Recombinant Human Interleukin–2 and Decarbazine in Metastatic Melanoma: A Multicenter Phase II Study, Stoter, et al., *Journal of Clinical Oncology*, 9: No. 9, 1687–1691, Sep. 1991.

Interactions between human monocytes and tumor cells, Monocytes can either enhance or inhibit the growth and survival of K562 Cells, Davies, et al., Nov. 1991.

Effects of Flavonoids on Immune and Inflammatory Cell Functions, Middleton, et al., *Biochemical Pharmacology*, 43: No. 6, 1167–1179, 1992.

Immunotherapy of mammary adenocarcinoma metastases in C3H/HeN mice with chronic administration of cyclo–oxygenase inhibitors alone or in combination with IL–2, Khoo, et al., *Clin. Exp. Metastasis*, 10: 239–252, 1992.

Oxygen Free Radical Generation and Regulation of Proliferative Activity of Human Mononuclear Cells Responding to Different Mitogens, Whitacre, et al., *Cellular Immunology*, 144: 287–295, 1992.

A phase II study of interleukin–2 and Interferon–alpha in head and neck cancer, Schantz, et al., *Investigational New Drugs*, 10: 217–223, 1992.

Regulation of the Natural Killer Cell Response to Interleukin–α by Biogenic Amines. Hellstrand, et al., *Journal of Interferon Research*, 12: 199–206, 1992.

A Randomized Phase II Trial of Continuous Infusion Interleukin–2 or Bolus Injection Interleukin–2 Plus Lymphokine–Activated Killer Cells for Advanced Renal Cell Carcinoma, Weiss, et al., *Journal of Clinical Oncology*, 10: No. 2, 275–281, Feb. 1992.

Natural Killer (NK) Cell Stimulatory Factor Increases the Cytotoxic Activity of NK Cells from Both Healthy Donors and Human Immunodeficiency Virus–infected Patients, Chehimi, et al., *Journal of Experimental Medicine*, 175: 789–796, Mar. 1992.

Chemoimmunotherapy of Metastatic Murine Renal Cell Carcinoma Using Flavone Acetic Acid and Interleukin–2, Salup, et al., *The Journal of Virology*, 147: 1120–1123, Apr. 1992.

Phase I Trial of High–Dose Bolus Interleukin–2 and Interferon Alfa–2a in Patients with Metastatic Malignancy, Budd, et al., *Journal of Clinical Oncology*, 10: No. 5, 804–809, May 1992.

Prolonged Continuous Intravenous Infusion Interleukin–2 and Lymphokine–Activated Killer–Cell Therapy for Metastatic Renal Cell Carcinoma, Thompson, et al., *Journal of Clinical Oncology*, 10: No. 6, 960–968, Jun. 1992.

Phase II Study of Subcutaneous Interleukin–2 in Unselected Patients With Advanced Renal Cell Cancer on an Outpatient Basis, Sleijfer, et al., *Journal of Clinical Oncology*, 10: No. 7, 1119–1123, Jul. 1992.

A Phase II Trial of Interleukin–2 and Interferon Alfa–2a in Patients With Advanced Renal Cell Carcinoma Ilson, et al., *Journal of Clinical Oncology*, 10: No. 7, 1124–1130, Jul. 1992.

Effects of Cancer Immunotherapy with Indomethacin and Interleukin–2 on Murine Hemopoietic Stem Cells, Saarloos, et al., *Cancer Research*, 52: 6452–6462, Dec. 1, 1992.

Effects of histamine type–2 receptor antagonists on indomethacin and IL–2 immunotherapy of metastasis Saarloos, et al., *Clin. Exp. Metastasis*, 11: 275–283, 1993.

Serotonergic 5–$HT_{14}$ Receptors Regulate a Cell Contact–Mediated Interaction between Natural Killer Cells and Monocytes, Hellstrand, et al., *Scand J. Immunol.* 37: 7–18, 1993.

Sustained Indomethacin and Ranitidine with Intermittent Continuous Infusion Interleukin–2 in Advanced Malignant Melanoma: A Phase II Study, Mertens, et al., *Clinical Oncology*, 5: No. 2, 107–113, 1993.

"Induction of lymphokine activated killer cells in serum–free medium" Froelich, et al., *Journal of Immunological Methods*, 86:205–211, No. 2 (1986).

"Peptide derivative cytochrome inhibit enzyme system oxidation burst phagocyte cell inflammation disease" Malech, et al., DABASE WPI/DERWENT (Abstract) Jul. 25, 1989.

"Histaminergic Regulation of NK Cells" Hellstrand, et al., *Journal of Immunology,* 153:4940–4947, No. 11, Dec. 1, 1994.

Lasek, et al., "Potentiation of antitumor effects of tumor necrosis factor α and interferon γ by macrophage–colony–stimulating in a MnB16 melanoma model in mice" *Cancer Immunol Immunother* 40:315–321 (1995).

Sone, et al., "Tumor cytotoxicity and interleukin 1 production of blood monocytes of lung cancer patients" *Cancer Immunol Immunother.* 30:357–362 (1990).

ENHANCED ACTIVATION OF NATURAL KILLER CELLS USING AN NK CELL ACTIVATOR AND A HYDROGEN PEROXIDE SCAVENGER OR INHIBITOR

CROSS REFERENCE TO RELATED APPLICATIONS

This application is a continuation of U.S. patent application Ser. No. 08/287,200, filed Aug. 8, 1994 now abandoned. This application is related to U.S. application Ser. No. 07/843,052, filed Mar. 2, 1992, now U.S. Pat. No. 5,348,739.

FIELD OF THE INVENTION

The present invention relates generally to methods for the enhanced activation of natural killer (NK) cells, useful for example, in the treatment of cancer and viral infection. More specifically, the present invention relates to the activation of NK cells using a combination of a natural killer cell activator and a hydrogen peroxide inhibiting compound or scavenger. It also relates to the prevention of inactivation of NK cells.

BACKGROUND OF THE INVENTION

Natural killer (NK) cells are a subset of spontaneously cytotoxic lymphocytes that lytically destroy tumor cells without apparent antigen specificity or restriction by histocompatibility molecules. Lymphokines are lymphocyte-derived peptides that modulate immunologic and inflammatory responses by regulating the activity, growth and differentiation of a wide variety of leukocyte and nonleukocyte target cells. Similar factors produced by a variety of cell types, together with lymphokines, are known as cytokines. Several cytokines are known to stimulate proliferation of NK cells and to enhance their cytotoxic activity.

Interleukin-2 (IL-2), formerly T-cell growth factor (TCGF), is a T-cell-derived cytokine. Since 1985, IL-2 has been used in the treatment of human neoplasia, mainly in patients with metastasizing solid tumors, such as malignant melanoma and renal cell carcinoma (Rosenberg et al., N. Engl. J. Med. 316:889–897 (1987); Bukowski et al., J. Clin. Oncol. 7:477–485 (1989)), but more recently also in acute myelogenous leukemia (AML) (Foa et al., Br. J. Haematol. 77:491–496.3 (1991)). In the initial studies, IL-2 was administered together with autologous lymphocytes that had been treated with IL-2 in vitro, but in recent years IL-2 has more frequently been administered as a single agent.

The high expectations for the treatment of human cancer using IL-2 were based on the findings that treatment with IL-2 can induce the regression of established tumors in several animal tumor models in vivo (Rosenberg et al., J. Exp. Med. 161:1169–1188 (1985); Lotre and Rosenberg, in Interleukin-2, K. A. Smith, ed., Academic Press, San Diego, pp. 237–294 (1988)). The mechanism underlying this anti-tumor effect of IL-2 has been much debated, but accumulating evidence points to the anti-tumor effector cell as the natural killer (NK)-cell. Depletion of NK cells from experimental animals eliminates the anti-tumor effect of IL-2 in many experimental models for tumor growth and metastasis (Mule et al., J. Immunol. 139:285 (1987)). Further, the only subset of resting human peripheral blood lymphocytes that carry transducing receptors for IL-2 (IL-2R) on the cell surface are NK cells (Caliguri et al., J. Clin. Invest. 91:123–132 (1993)).

IL-2 activates many NK-cell functions, including baseline or "natural" anti-tumor cytotoxicity, antibody-dependent cellular cytotoxicity (ADCC), proliferation, and cytokine production (Trinchieri, Adv. Immunol. 47:187–376 (1989)). Also, IL-2-activated NK cells, frequently referred to as lymphokine-activated killer (LAK) cells, display a broader spectrum of reactivity against human and murine tumor target cells. Thus, NK cells activated by IL-2 not only kill NK cell-sensitive tumor cells more efficiently, but also kill tumor cells that are insensitive to the constitutive cytotoxic activity mediated by NK cells.

Recent studies have also shown that IL-2, when combined with histamine or serotonin, augments NK cell cytotoxicity in the presence of monocytes in vitro (Hellstrand et al., J. Immunol. 145(12):4365–4370 (1990) and Hellstrand et al., Scand. J. Immunol. 32(2):183–192 (1990)). These studies suggest an interaction between monocytes and NK cells that is subject to regulation by these biogenic amines (Hellstrand et al., J. Interferon Rsch. 12:199–206 (1992). These NK cell regulating mechanisms are thus believed to be of importance to the NK cell mediated response to metastatic tumors in vivo.

Despite the beneficial effects obtained with IL-2 therapy in experimental animals and despite the remarkable effects of IL-2 on the killing activity of human NK cells in vitro, the results of the clinical trials of IL-2 in human cancer have, as yet, been disappointing. Only a small fraction of patients with metastatic melanoma or renal cell carcinoma show objective regression of tumor burden after treatment with very high doses of IL-2 (Bukowski et al., J. Clin. Oncol. 7:477–485 (1989); Whitehead et al., J. Natl. Cancer Inst. 83:1250–1253 (1991)). In addition, IL-2 produces severe side effects, including hypotension, fluid retention ("capillary leak syndrome"), fever, lethargy and nausea.

Other interleukins are also known to stimulate NK cell activity. For example, IL-12, also known as natural killer cell stimulatory factor (NKSF), is a recently discovered cytokine which has also been reported to increase NK cell and cytotoxic T lymphocyte activity, T cell proliferation, and the production of interferon-γ. It has been found to enhance the spontaneous cytotoxic activity of peripheral blood lymphocytes against a variety of tumor-derived target cell lines (Chehimi et al., J Exp. Med. 175:789–796 (1992)). IL-1 is another cytokine known to enhance NK cell cytotoxicity.

The interferons consist of a family of secreted proteins with potent antiproliferative and immunomodulatory activities. These immunomodulatory effects include activation of macrophages, augmentation of cellular and humoral immune responses, and enhancement of NK-cell activity. All three major subtypes of human interferon, i.e., interferon-α (IFN-α), interferon-β (IFN-β) and interferon-γ (IFN-γ), are known to enhance NK cell cytotoxicity. Interferon-α (IFN-α) is a major regulatory factor for NK cells. It has been found to stimulate NK cells (Silva et al., J. Immunol. 125:479–484 (1980)) and augment NK cell cytotoxicity both in vitro and in vivo (Trinchieri, Adv. Immunol. 47:187–376 (1989)). Although IFN-α has been shown to be effective with some neoplasias, the overall results of therapy with high doses of IFN-α have been disappointing. In addition, patients treated with IFN-α often have acute toxic reactions including fever, chills, myalgias, anorexia, fatigue, headache, nausea and vomiting.

Other known stimulators of NK cell activity include certain flavonoids. The flavonoids are a group of low molecular weight polyphenolic secondary plant metabolites. Flavone-8-acetic acid has been found to potently augment NK activity in the spleen, liver, lungs, and peritoneum (Wiltrout et al., J. Immunol. 140(9):3261–3265 (1988)). Xanthenone-4-acetic acid (XAA), an analog of FAA, and its methyl-substituted derivatives, have also been found to induce NK activity in vitro (Ching et al., Eur. J. Cancer 27(1):79–83 (1991)). Clinical trials of FAA have been disappointing, however, due to non-linear pharmokinetics, low dose potency and problems of drug precipitation.

SUMMARY OF THE INVENTION

The present invention provides a novel method for the activation of NK cells and the prevention of inactivation of these cells by monocytes, using a combination of a lymphokine or other NK cell activator and a peroxide reducing or scavenging compound. The present invention is especially useful in the treatment of solid tumors and viral infection.

In accordance with one aspect of the present invention, there is provided a method for providing activated natural killer cells comprising the steps of administering to a population of cells which includes lymphocytes and monocytes, an effective amount of an NK cell activating compound and a compound effective to inhibit the production or release of intracellular hydrogen peroxide, provided that when said NK cell activating compound is IL-2 or IFN-α, said compound effective to inhibit the production or release of intracellular hydrogen peroxide is not histamine, an $H_2$ receptor agonist or serotonin.

In a preferred embodiment of the present invention, the compound effective to inhibit the production or release of intracellular hydrogen peroxide is histamine, an $H_2$ receptor agonist or serotonin, and the NK cell activating compound is a cytokine or a flavonoid. In another preferred embodiment, the population of cells is located in vivo. In still another preferred embodiment, the administration of said NK cell activating compound and said compound effective to inhibit the production or release of intracellular hydrogen peroxide is performed simultaneously. Alternatively, the administration of said NK cell activating compound and said compound effective to inhibit the production or release of intracellular hydrogen peroxide is performed within 24 hours.

In another preferred embodiment of the present invention, the NK cell activating compound is a cytokine, which is administered in a dose of from about 1,000 to about 300,000 U/kg/day. In the preferred embodiment wherein the NK cell activating compound is a flavonoid, the flavonoid is administered in a dose of from about 1 to about 100,000 mg/day. In still another preferred embodiment, the compound effective to inhibit the production or release of intracellular hydrogen peroxide is administered in a dose of from about 0.1 to about 10 mg/day.

In accordance with another aspect of the present invention, there is provided a method for providing activated natural killer cells comprising the steps of administering to a population of cells which includes lymphocytes and monocytes, an effective amount of an NK cell activating compound and administering a hydrogen peroxide scavenger. In a preferred embodiment, the hydrogen peroxide scavenger catalyzes the decomposition of hydrogen peroxide. In a preferred embodiment, the hydrogen peroxide scavenger is catalase, glutathione peroxidase, or ascorbate peroxidase. In another preferred embodiment, the NK cell activating compound is a cytokine or a flavonoid. In still another preferred embodiment, the population of cells is located in vivo.

The administration of said NK cell activating compound and said hydrogen peroxide scavenger is preferably performed simultaneously. Alternatively, the administration of said NK cell activating compound and said hydrogen peroxide scavenger is performed within 24 hours. In a preferred embodiment, the NK cell activating compound is a cytokine, and the cytokine is administered in a dose of from about 1,000 to about 300,000 U/kg/day. In the preferred embodiment wherein the NK cell activating compound is a flavonoid, the flavonoid is administered in a dose of from about 1 to about 100,000 mg/day. Preferably, the hydrogen peroxide scavenger is administered in a dose of from about 0.1 to about 10 mg/day.

DESCRIPTION OF THE DRAWINGS

FIG. 3 shows the inhibition of IL-2-induced NK cell proliferation and cytotoxicity by monocytes and its reversal by histamine and catalase. Culture medium (open bars), histamine (hatched bars), and catalase (filled bars) were added to enriched NK cells (NK) or a mixture of NK cells and monocytes (NK+MO).

DETAILED DESCRIPTION OF THE INVENTION

Figure 1A:
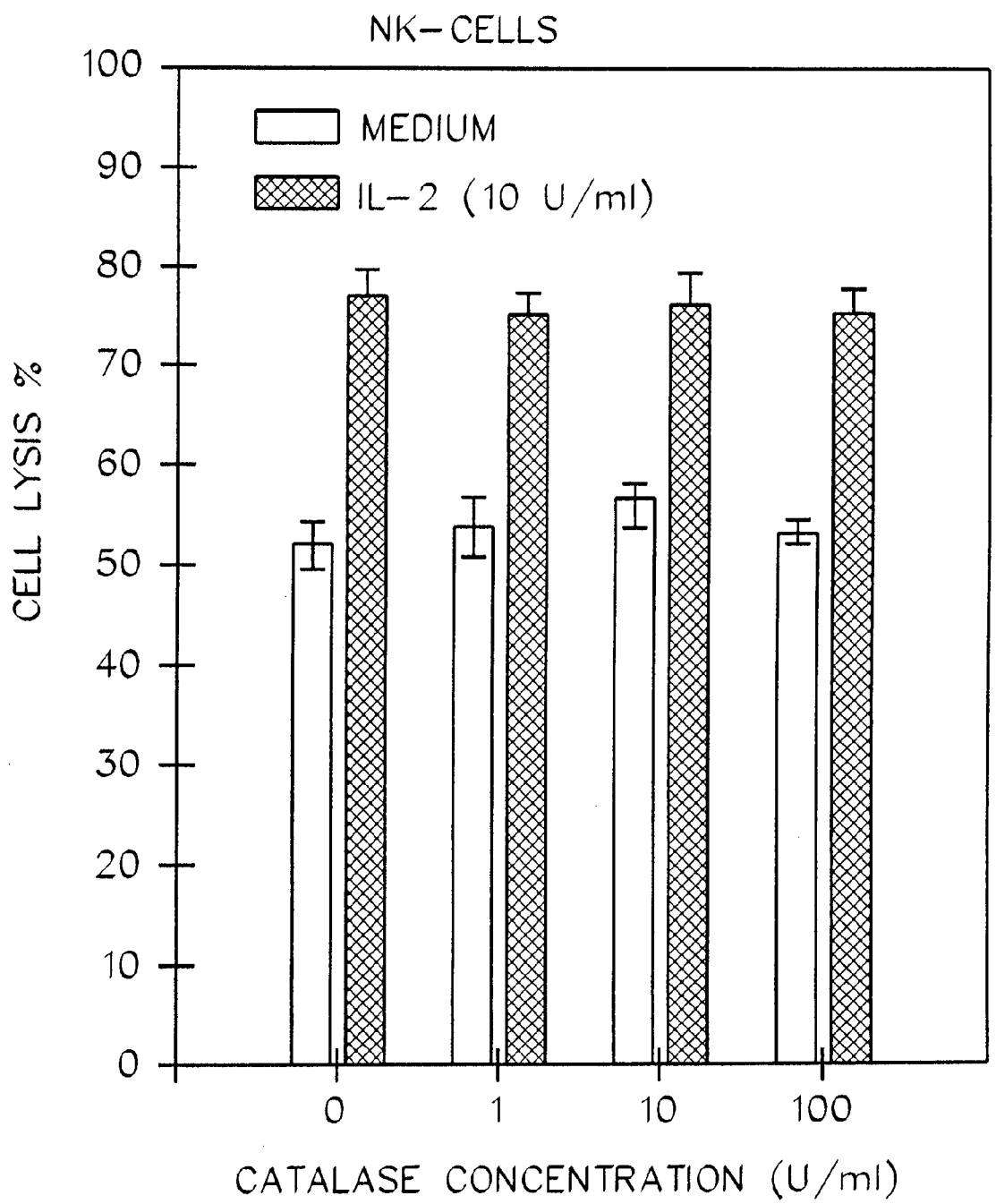
FIG. 1 graphically depicts the activation of NK cells by catalase and synergy with IL-2. Culture medium (control; open bars) or IL-2 (10 U/ml; filled bars) was added to enriched human NK cells alone (FIG. 1A) or NK cells admixed with 30% monocytes (FIG. 1B) in the presence of catalase at the indicated final concentrations. The bars indicate NK cell-mediated killing of target tumor cells (cell lysis %±s.e.m. of sextuplicate determination).

The present invention relates to a method for activating NK cells in the presence of monocytes by using a hydrogen peroxide inhibiting or scavenging compound in combination with a cytokine or other NK cell activator. The method of the present invention is useful, for example, as a method of inhibiting tumor growth and the formation of metastases of malignant tumor cells, and in the treatment of viral infection.

In the monovalent pathway of oxygen reduction, superoxide anion ($O_2^{31}$) is produced first, followed by the formation of hydrogen peroxide ($H_2O_2$). Superoxide anion can react with hydrogen peroxide to form hydroxyl radical (OH). These reactive oxygen intermediates (ROI) are produced by phagocytes such as monocytes and polymorphonuclear neutrophils (PMNs). Hydrogen peroxide produced by monocytes has been found to suppress NK cell mediated cytotoxicity. This NK cell cytotoxicity plays an important role in a host's defenses against arising neoplasms and metastatic tumor cells in vivo. It has now been discovered that monocytes suppress NK cell cytotoxicity and that this monocyte derived suppressive signal effectively down-regulates the cytotoxic and proliferative activities of NK cells. Suppression of NK cells has been found to be halted in the presence of the biogenic amines histamine and serotonin (Hellstrand et al., *J. Immunol.* 145:4365–4370 (1990)).

It is one of the surprising discoveries of the present invention that compounds which reduce the amount of hydrogen peroxide, when administered in combination with a cytokine or other compound known to stimulate NK cell activity, act to synergistically stimulate NK cell cytotoxicity in the presence of monocytes; thus, the administration of scavengers of peroxide, or compounds which inhibit the production or release of intracellular peroxide, in combination with a cytokine or other NK cell activator, has been found effective in the treatment of solid tumors and viral infection.

Known scavengers of hydrogen peroxide include the enzymes catalase, glutathione peroxidase and ascorbate peroxidase. Compounds which inhibit the production or the release of intracellular peroxide are also effective in enhancing NK cell activity when administered together with an NK cell activator. Such compounds include serotonin, histamine, and $H_2$ receptor agonists such as dimaprit.

The present invention therefore provides an effective method for preventing the inactivation of NK cells and for activation these cells. It also provides a method for treatment of tumors and viral infection, through the administration of compounds which reduce the amount of hydrogen peroxide, in combination with a cytokine or other compound known to stimulate NK cell activity. It is intended that the present invention cover the administration of the compounds listed and those compounds with similar activity, with the understanding that if the cytokine administered is IL-2 or IFN-α, the inhibitor is not histamine, an $H_2$ receptor agonist, or serotonin.

Administration of NK Cell Activator and Hydrogen Peroxide Scavenger or Inhibitor The administration of the cytokine or other compound known to enhance NK cell activity, together with the inhibiting or scavenging compounds discussed above, can be by any of a number of methods well known to those of skill in the art. Such methods include the parenteral delivery through intravenous, intraperitoneal, or intramuscular injection. The NK cell activity enhancer and the hydrogen peroxide scavenger can be administered separately or as a single composition. When administered separately, it is contemplated that the NK cell activity enhancer may be administered either first or last.

The compounds of the present invention may be administered in water with or without a surfactant such as hydroxypropyl cellulose. Dispersions are also contemplated, such as those utilizing glycerol, liquid polyethylene glycols, and oils. Antimicrobial compounds may also be added to the preparations. Injectable preparations may include sterile aqueous solutions or dispersions and powders which may be diluted or suspended in a sterile environment prior to use. Carriers such as solvents or dispersion media contain water, ethanol polyols, vegetable oils and the like may also be added to the compounds of the present invention. Coatings such as lecithins and surfactants may be used to maintain the proper fluidity of the composition. Isotonic agents such as sugars or sodium chloride may be added, as well as products intended to delay absorption of the active compounds such as aluminum monostearate and gelatin. Sterile injectable solutions are prepared according to methods well known to those of skill in the art and can be filtered prior to storage and/or use. Sterile powders may be vacuum or freeze dried from a solution or suspension them. Sustained-release preparations and formulations are also contemplated by the present invention. Any material used in the composition of the present invention should be pharmaceutically acceptable and substantially non-toxic in the amounts employed.

All preparations may be provided in dosage unit forms for uniform dosage and ease of administration. Each dosage unit form contains a predetermined quantity of active ingredient calculated to produce a desired effect in association with an amount of pharmaceutically acceptable carrier.

Although in the Examples which follow the compounds are administered as a single dose, it should be understood that the compounds may be administered for prolonged periods of time. Typically, the treatment may be administered for periods up to about one week, and even for periods longer than one month. In some instances, the treatment may be discontinued and then resumed at a later time. A daily dose may be administered as a single dose, or it can be divided into several doses, especially if negative effects are observed. In addition, the compounds of the present invention can be administered as a single composition, or separately. If administered separately, the compounds should be given on the same day, such that the activation of NK cells by the lymphokine or other compound is enhanced.

Preferred dosage range can be determined using techniques known to those having ordinary skill in the art. IL-1, IL-2 or IL-12 can be administered in an amount of from about 1,000 to about 300,000 U/kg/day; more preferable, the amount is from about 3,000 to about 100,000 U/kg/day, and even more preferably, the amount is from about 5,000 to about 20,000 U/kg/day.

IFN-α, IFN-β, and IFN-γ can also be administered in an amount of from about 1,000 to about 300,000 U/kg/day; more preferable, the amount is from about 3,000 to about 100,000 U/kg/day, and even more preferably, the amount is from about 10,000 to about 50,000 U/kg/day.

Flavonoid compounds can be administered in an amount of from about 1 to about 100,000 mg/day; more preferable, the amount is from about 5 to about 10,000 mg/day, and even more preferably, the amount is from about 50 to about 1,000 mg/day.

Compounds which inhibit the release or formation of intracellular hydrogen peroxide, or scavengers of hydrogen peroxide, can be administered in an amount of from about 0.1 to about 10 mg/day; more preferable, the amount is from about 0.5 to about 8 mg/day, and even more preferably, the amount is from about 1 to about 5 mg/day. However, in each case, the dose depends on the activity of the administered compound. The foregoing doses are appropriate for histamine, catalase and for $H_2$ receptor agonists. Appropriate doses for any particular host can be readily determined by empirical techniques well known to those of ordinary skill in the art.

The method of the present invention may be utilized alone or in combination with other anti-cancer therapies, as determined by the practitioner.

Monocyte-Induced Inhibition of NK Cells: Reversal by Catalase and the Role of Reactive Oxygen and Nitrogen Species To investigate the effects of hydrogen peroxide scavengers on the activation of NK cells by cytokines, we studied the effects of catalase, a heme containing enzyme that catabolizes hydrogen peroxide ($H_2O_2$) to oxygen and water, on human NK cell-mediated killing of tumor cells in vitro and on NK cell function in mice in vivo. These experiments are described below in Examples 1 and 2. The following examples are merely illustrative of the present invention, and are not intended to limit the invention in any way.

EXAMPLE 1

Using blood obtained from a healthy human blood donor, we studied the effects of catalase on NK cell-mediated killing of tumor cells. K562 cells, from an NK sensitive erythroleukemic cell line, were used as target cells in all experiments. Washed cells ($10\times10^6$ cells/ml) were incubated with $^{51}$Cr (Amersham) at a concentration of 150 µCi/ml cell suspension for 2–4 hours. After centrifugation and resuspension in cell culture medium, $10^4$ cells in 50 µl portions were added to the effector cells in microplate wells.

In the first set of experiments, human NK cells alone ($1.5\times10^5$ cells/well) were added to the K562 target cells. The combined cells were then exposed to culture medium (control) or human recombinant IL-2 (EuroCetus, Amsterdam, The Netherlands) at a final concentration of 10 U/ml. The cells were then exposed to catalase (Boehringer-Mannheim) at concentrations of 0 to 100 U/ml. These same conditions were repeated using human NK cells admixed with 30% human peripheral blood monocytes, recovered by centrifugal elutriation, added to the target K562 cells.

Figure 1B:
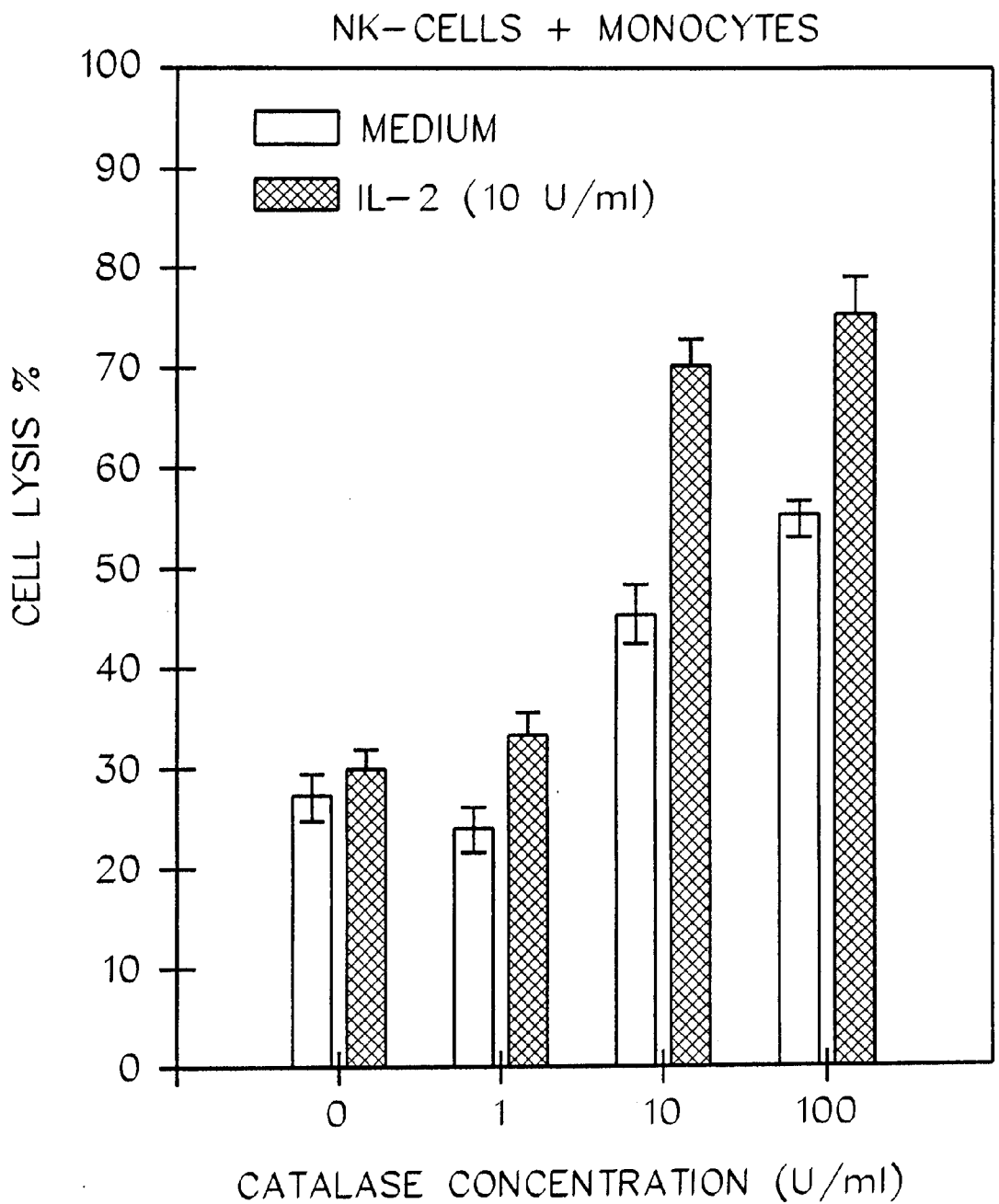

After incubation at 37° C. for 16 hours, supernatant fluids were collected by a tissue collecting system (Amersham) and assayed for radioactivity in a gamma counter. Maximum $^{51}$Cr release was determined in target cell cultures treated with Triton-X. NK cell cytotoxicity was calculated as cell lysis % according to the following formula:

cell lysis %=100×experimental release−spontaneous release/maximum release−spontaneous release The results of these studies are illustrated in FIG. 1. FIG. 1A shows that catalase does not affect the level of NK-cell-mediated killing of tumor cells in the absence of monocytes, regardless of whether the NK cells are unactivated or activated by IL-2. FIG. 1B shows that the anti-tumor activity of unactivated NK cells is suppressed by the presence of monocytes. Further, catalase, at final concentrations exceeding 10 U/ml, reverses this suppressive signal. FIG. 1A further shows that IL-2 does not significantly activate NK-cell cytotoxicity against tumor cells in the presence of monocytes unless catalase is present.

Effects of Catalase and Other Scavengers

To study the relationship between the monocyte-derived inhibitory signal and the respiratory burst activity of monocytes, we added catalase and various other scavengers of reactive oxygen metabolites to NK cells, alone or admixed with monocytes. We then measured the cytotoxicity of the NK cells against NK cell sensitive K562 target cells as described above. The results of this testing are shown in Table I.

TABLE I

Effect of scavengers of reactive oxygen and nitrogen metabolites on monocyte-induced inhibition of NK-cell cytotoxicity.

| exp. no. | treatment | conc. | MO | cell lysis %[a] medium | histamine |
|---|---|---|---|---|---|
| 1 | catalase | 0 | − | 55 ± 3 | 53 ± 2 |
|  | " | 20 U/ml | − | 60 ± 3 | 52 ± 4 |
|  | " | 0 | + | 19 ± 2 | 57 ± 1 |
|  | " | 2.5 U/ml | + | 21 ± 1 | 55 ± 2 |
|  | " | 5 U/ml | + | 34 ± 2 | 55 ± 2 |
|  | " | 10 U/ml | + | 49 ± 1 | 52 ± 2 |
|  | " | 20 U/ml | + | 57 ± 2 | 50 ± 4 |
|  | SOD | 200 U/ml | − | 52 ± 2 | 54 ± 2 |
|  | " | 200 U/ml | + | 1.3 ± 2 | 54 ± 2 |
| 2 | taurin | 0 | − | 72 ± 2 | 70 ± 3 |
|  | " | $10^{-3}$ M | − | 70 ± 4 | 75 ± 4 |
|  | " | 0 | + | 6 ± 2 | 63 ± 4 |
|  | " | $10^{-3}$ M | + | 6 ± 1 | 64 ± 3 |
| 3 | deferox | 0 | − | 79 ± 4 | 78 ± 2 |
|  | " | $10^{-4}$ M | − | 81 ± 2 | 74 ± 5 |
|  | " | 0 | + | 9 ± 3 | 62 ± 2 |
|  | " | $10^{-4}$ M | + | 12 ± 3 | 60 ± 2 |
| 4 | mannitol | 0 | − | 77 ± 4 | 69 ± 2 |
|  | " | $3 \times 10^{-4}$ M | − | 73 ± 3 | 68 ± 3 |
|  | " | 0 | + | 19 ± 2 | 64 ± 4 |
|  | " | $3 \times 10^{-4}$ M | + | 20 ± 1 | 67 ± 2 |
| 5 | L-NMMA | 0 | − | 58 ± 1 | 51 ± 2 |
|  | " | $2 \times 10^{-4}$ M | − | 61 ± 3 | 54 ± 2 |
|  | " | 0 | + | 12 ± 1 | 45 ± 2 |
|  | " | $2 \times 10^{-4}$ M | + | 11 ± 1 | 45 ± 3 |

[a]NK-cell-enriched lymphocytes treated with culture medium (control), histamine ($10^{-4}$ M), and catalase, SOD, taurin, mannitol, deferoxamine (deferox), or L-NMMA at indicated final concentrations in the presence (MO+) or absence (MO−) of monocytes. All components were added at the onset of a microcytotoxicity assay against K 562 target cells. Data are cell lysis % ± s.e.m. of sextuplicates and show results from five separate experiments.

Catalase, which effectively degrades $H_2O_2$, had no effect on the cytotoxicity of NK cells in the absence of monocytes but was found to completely abrogate the monocyte-induced inhibition of baseline NK cell cytotoxicity. Catalase was effective at concentrations exceeding 5 U/ml. Histamine (histamine dihydrochloride; Sigma) at concentrations exceeding $10^{-7}$ M abrogated the monocyte induced suppression of NK cells but was ineffective in the presence of catalase.

It was also discovered that superoxide dismutase (SOD), a scavenger of $O_2^-$, did not alter the suppressive effect of monocytes on NK cells over a wide range of concentrations. Similarly, taurin, a scavenger of HOCl⁻, and scavengers of OH such as mannitol and deferoxamine, were ineffective at reducing the suppressive effects of monocytes on NK cells.

Further, monocytes and macrophages produce reactive nitrogen intermediates of which nitric oxide (NO) is the ultimate effector molecule. To study whether NO induction in monocytes contributed to NK cell inhibition, we used a NO synthetase inhibitor, N-monomethyl-L-arginine (L-NMMA). This compound, used at concentrations sufficient to inhibit induction of NO in monocytes, did not alter the suppression of NK cell function by monocytes. These results are also shown in Table I.

Thus, we have concluded that NK cell-mediated cytotoxicity is suppressed by $H_2O_2$ produced by monocytes. This suppression of NK cell-mediated cytotoxicity induced by $H_2O_2$ is abrogated by the presence of catalase or histamine. In addition, it was discovered that human NK cells do not respond to IL-2 unless the monocyte-derived $H_2O_2$ is scavenged by catalase or by some other scavenger.

In vivo Effects of Hydrogen Peroxide Scavengers

To study whether the regulatory effects on human NK cell function induced by catalase in vitro are of importance for NK cell-mediated killing of tumor cells in vivo, experiments were performed in which catalase was injected intravenously to mice shortly before intravenous inoculation of NK cell-sensitive tumor cells. These experiments are described below in Example 2.

EXAMPLE 2

Seventy-five thousand $^{51}$Cr-labeled, NK cell-sensitive YAC-1 mouse lymphoma cells were injected intravenously into male or female 4 to 6 week old Swiss Albino mice, together with vehicle (control) or 100 U/kg catalase. Two hours after inoculation with the tumor cells, the mice were sacrificed by cervical dislocation. The lungs were removed and placed in test tubes in a gamma-counter, and the radioactivity in the lung tissue was measured. The radioactivity in lung tissue is an inverse measure of NK cell-mediated killing of tumor cells in vivo (see Hanna et al., JNCI 65:801 (1980)), and is expressed as a percent of the $^{51}$Cr that is retained in lungs immediately after inoculation of radiolabeled tumor cells.

Figure 2:
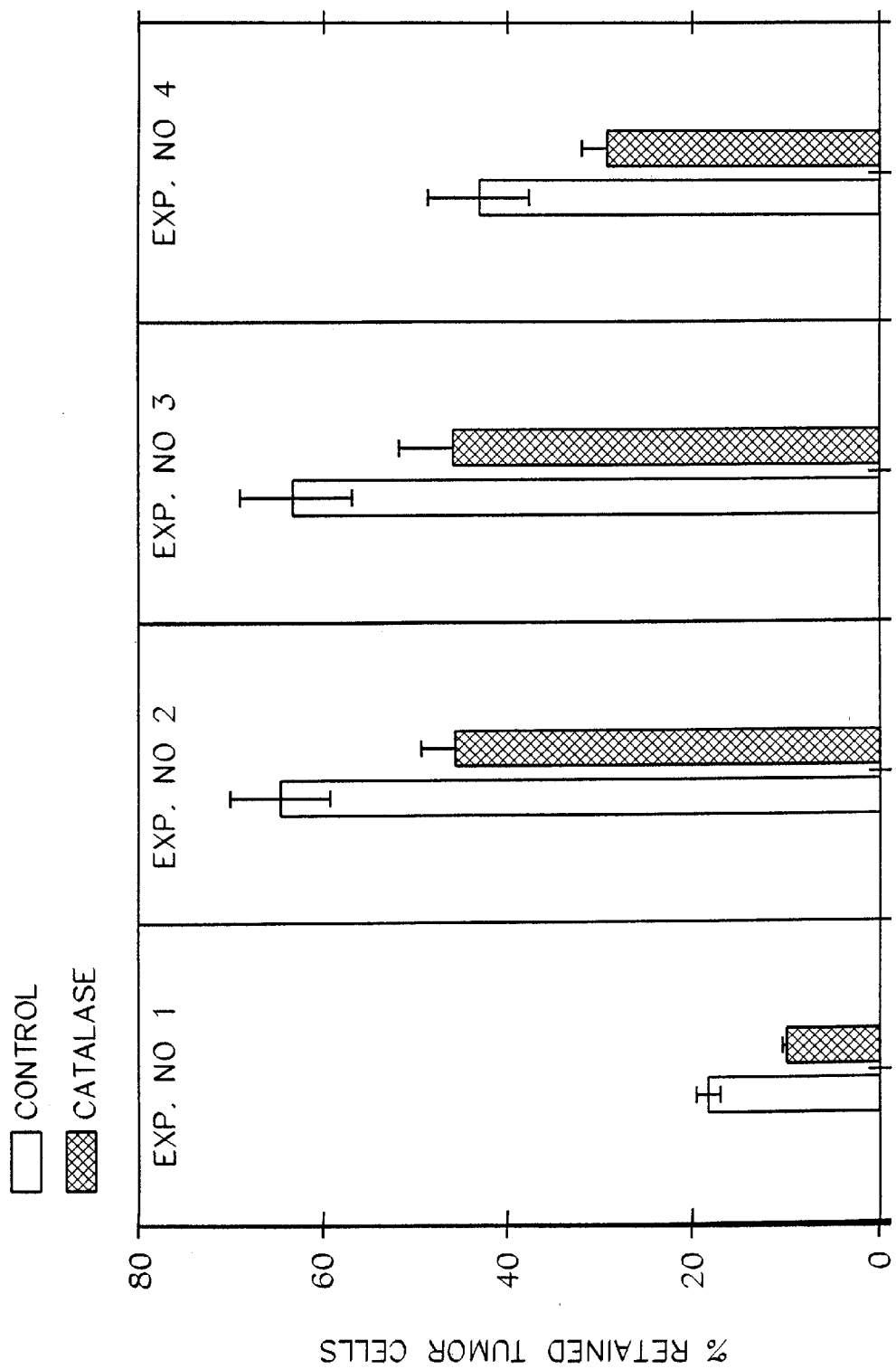
FIG. 2 graphically depicts the activation of NK cell-mediated clearance of YAC-1 lymphoma cells in vivo by catalase. Seventy-five thousand YAC-1 cells labeled with $^{51}Cr$ were injected intravenously into male or female 4–6-week-old Swiss Albino mice, together with vehicle (control; open bars) or catalase (100 U/kg; filled bars). Two hours after the inoculation of tumor cells, the mice were sacrificed by cervical dislocation. The results show retained radioactivity in lung tissue (% of radioactivity retained in lungs at t=0 after injection of labeled tumor cells). Results from 4 separate experiments are shown. Each bar represents the mean±s.e.m. of 3–5 animals.

The results of this testing are shown in FIG. 2. The data in FIG. 2 represent four separate experiments. Each bar represents the retained radioactivity in lung pairs (mean ±s.e.m. of 3–5 animals). Consistently, it was found that treatment with catalase augmented the NK cell-mediated killing of YAC-1 lymphoma cells in vivo.

To determine whether the NK cell-mediated killing of tumor cells is enhanced using other NK cell activators and other peroxide scavengers, the experiments described below are performed.

EXAMPLE 3

The experiment described in Example 1 is repeated using IL-12 as the NK cell activator. Similar results are obtained.

EXAMPLE 4

The experiment described in Example 1 is repeated using IFN-α as the NK cell activator. Similar results are obtained.

EXAMPLE 5

The experiment described in Example 1 is repeated using FAA as the NK cell activator. Similar results are obtained.

EXAMPLE 6

The experiment described in Example 2 is repeated using glutathione peroxidase as the hydrogen peroxide scavenger. Similar results are obtained.

EXAMPLE 7

The experiment described in Example 2 is repeated using ascorbate peroxidase as the hydrogen peroxide scavenger. Similar results are obtained.

Inhibition of IL-2 Induced NK Cell Functions by Monocytes: Reversal by Catalase and Histamine IL-2 activates NK cell mediated cytotoxicity and induces proliferation of the resting population of NK cells. Elutriated monocytes effectively inhibit the IL-2 induced proliferation of enriched NK cells as well as the activation of NK cell cytotoxicity. To show that histamine, a compound we have discovered to suppress the generation of $H_2O_2$ in monocytes, and catalase, a scavenger of $H_2O_2$, reverse the monocyte-induced inhibition, the following experiments were performed.

EXAMPLE 8

Cell culture medium (control), histamine ($10^{-4}$ M), or catalase (20 U/ml), was added to either enriched NK cells alone or a mixture of NK cells and monocytes in microplates ($1.5\times10^5$ cells/well). Each group of cells then received 50 U/ml human recombinant IL-2 and were allowed to incubate for 48 hours. During the last 8 hours of incubation, cells were pulsed with $^3$H-methyl-thymidine (specific activity 2 Ci/mole; New England Nuclear Corp.; 1 $\mu$Ci/$2\times10^5$ cells). Following incubation, the cells were collected on glass fiber filters with an automatic cell harvester and cell-incorporated $^3$H-methyl-thymidine was estimated by liquid scintillography.

Figure 3A:
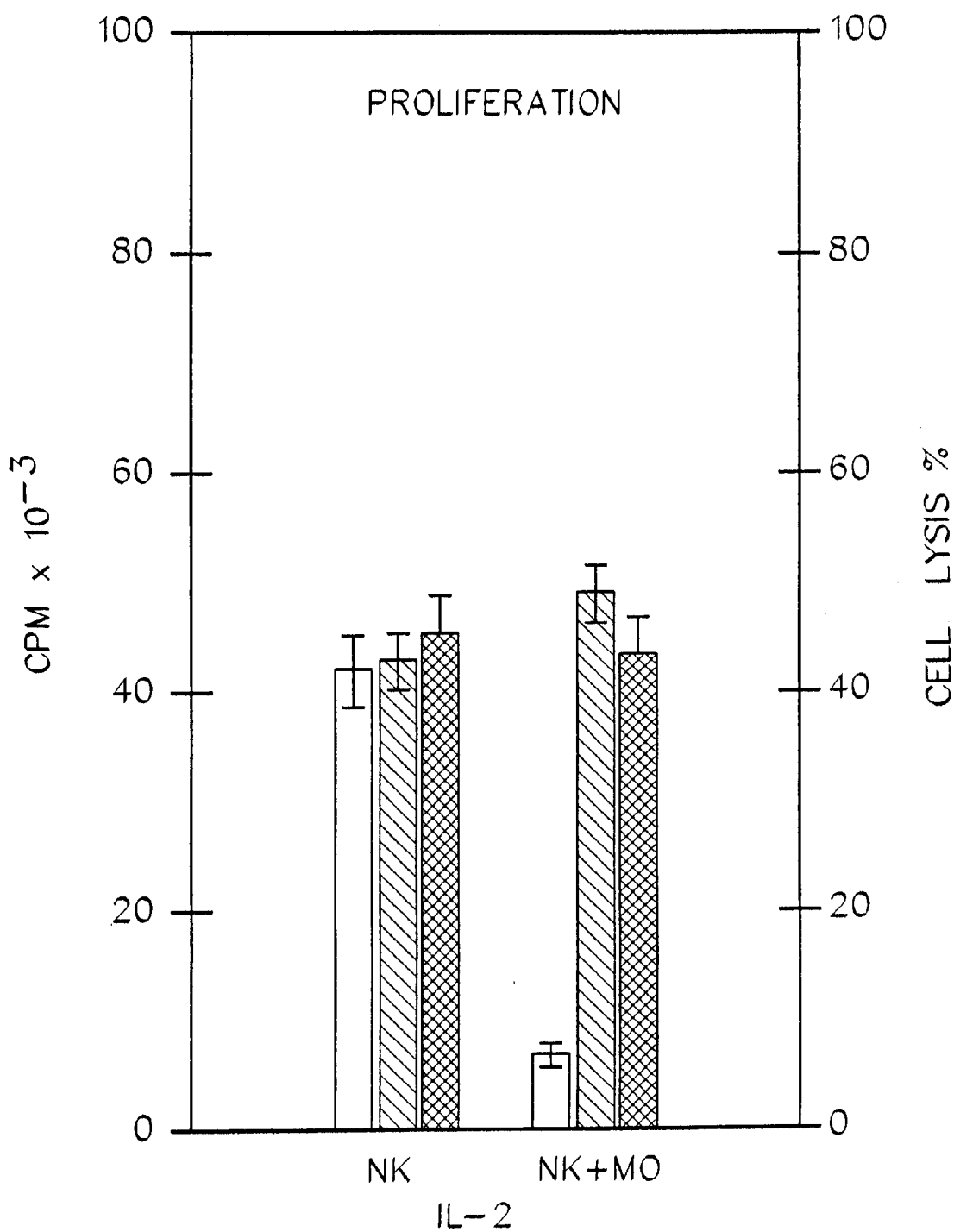
FIG. 3A shows NK cell proliferation.

The results are shown in FIG. 3A, which illustrates NK cell proliferation, as reflected by $^3$H-methyl-thymidine incorporation after treatment with IL-2. The bars represent cpm$\times10^3$ (proliferation) ±s.e.m. of sextuplicates. The results show that monocytes inhibit the proliferation of NK cells induced by IL-2. Both histamine and catalase effectively reverse this monocyte-induced inhibition.

To show the inhibitory effect of monocytes on IL-2 induced NK cell cytotoxicity, and its reversal by histamine and catalase, the following experiment was performed.

EXAMPLE 9

Cell culture medium (control), histamine ($10^{-4}$ M), or catalase (20 U/ml), was added to either enriched NK cells alone or a mixture of NK cells and monocytes ($1.5\times10^5$ cells/well). These mixtures were then incubated with K562 target cells in sextuplicate in microplates in a total volume of 200 $\mu$l and assayed for microcytotoxicity. After incubation at 37° C. for 16 hours in the presence of culture medium (control) or IL-2 (50 U/ml), supernatant fluids were collected and assayed for radioactivity as described above in connection with Example 1. The results are illustrated in FIG. 3B.

Figure 3B:
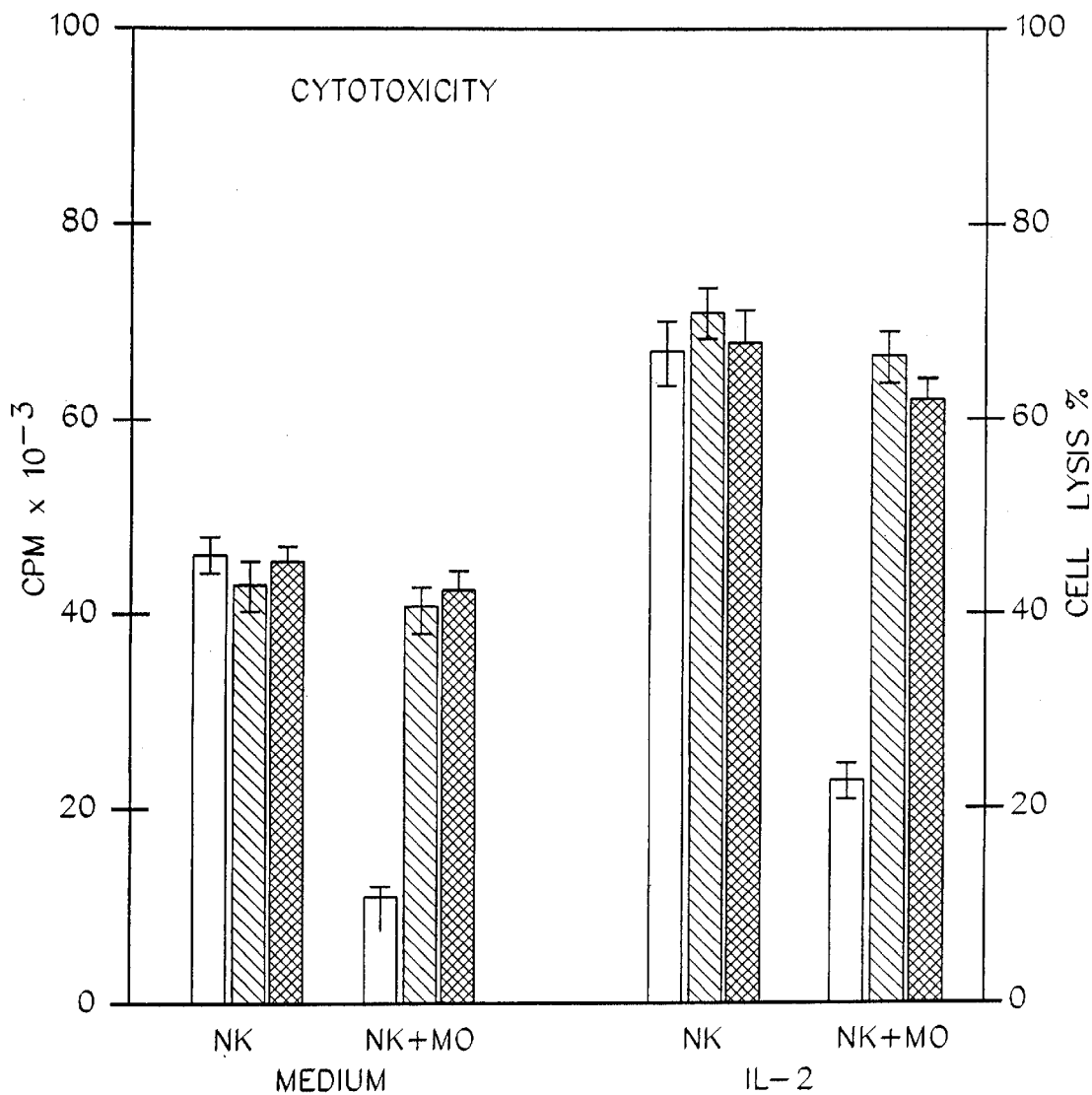
FIG. 3B shows cytotoxicity against K562 target cells.

FIG. 3B shows the cytotoxicity of the respective cell mixtures against K562 target cells. The bars represent percent cell lysis ±s.e.m. of sextuplicates. Again, it is clear from this data that monocytes inhibit the cytotoxicity of NK cells induced by IL-2. Both histamine and catalase effectively reverse this monocyte-induced inhibition.

Reconstitution of Monocyte Induced Inhibition by $H_2O_2$

The finding that catalase, but not scavengers of $O_2$ or of OH, reversed the suppression of NK cells by monocytes suggests that $H_2O_2$ or metabolites of this compound, is essential for expression of the inhibitory signal. We therefore studied whether hydrogen peroxide could reconstitute the inhibitory effects of monocytes on NK cells.

EXAMPLE 10

Figure 4:
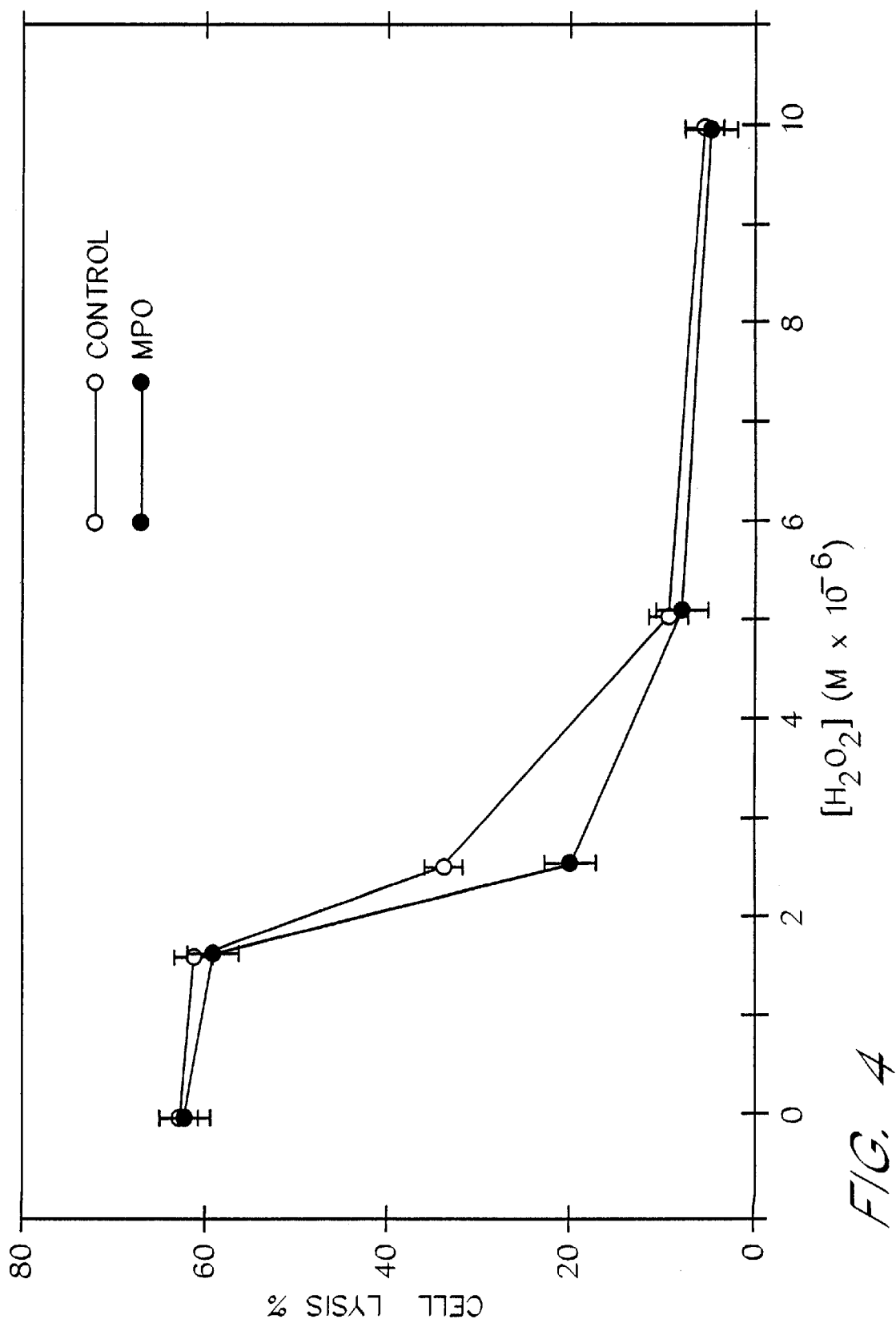
FIG. 4 illustrates the suppression of NK cell cytotoxicity by hydrogen peroxide and the role of myeloperoxidase. Open symbols represent the cytotoxicity of cells treated with hydrogen peroxide. Filled symbols represent corresponding cells treated with myeloperoxidase.

Culture medium (control) or $H_2O_2$ at concentrations between 0–10 $\mu$M was added to NK cell enriched lymphocytes for assay of cytotoxicity against $^{51}$Cr K562 target cells as described above. Addition of $H_2O_2$ to enriched NK cells effectively suppressed NK cell cytotoxicity. The results of this testing are shown in FIG. 4, which shows the cell lysis %±s.e.m. of sextuplicates. The $ED_{50}$ of $H_2O_2$ was approximately $2\times10^{-6}$ M, as seen in FIG. 4.

It was also discovered that catalase (20 U/ml), but not histamine, completely reversed the inhibition of NK cells induced by $H_2O_2$ (data not shown).

Role of MPO

To study whether $H_2O_2$ alone or its reactive metabolites mediated the inhibitory effect of exogenous $H_2O_2$ on NK cells, myeloperoxidase (MPO), a monocyte-derived enzyme that forms toxic hypohalous acids such as HOCl from $H_2O_2$, and halides and $OH^-$ from $H_2O_2$ and ferrous iron, was added to enriched NK cells, alone or together with $H_2O_2$. If radicals such as hypohalous acids contributed to the NK cell inhibitory signal, it was expected that MPO would potentiate the suppressive effect of $H_2O_2$ on enriched NK cells. This testing is described below in Example 11.

EXAMPLE 11

MPO (100 U/ml) and $H_2O_2$ at concentrations between 0–10 μM were added to NK cell enriched lymphocytes for assay of cytotoxicity against $^{51}Cr$ K562 target cells as described above. The results of this testing are shown in FIG. 4, which shows the cell lysis %±s.e.m. of sextuplicates.

MPO did not potentiate the suppressive effect of $H_2O_2$ on NK cells. It was found that addition of MPO slightly but significantly scavenged $H_2O_2$ in these experiments.

These results, along with the finding the mannitol, taurin and deferoxamine, all of which are scavengers of MPO catalyzed products, did not affect the inhibition of NK cells by monocytes suggested that the inhibitory signal is independent of MPO activity.

Kinetics of the Monocyte Derived NK Cell Inhibitory Signal

To assess when the inhibitory signal is conveyed from monocytes to NK cells, experiments were performed in which catalase or histamine were added to mixtures of monocytes and NK cells at various time points after the beginning of the microcytotoxicity assay against K562 target cells.

EXAMPLE 12

Figure 5:
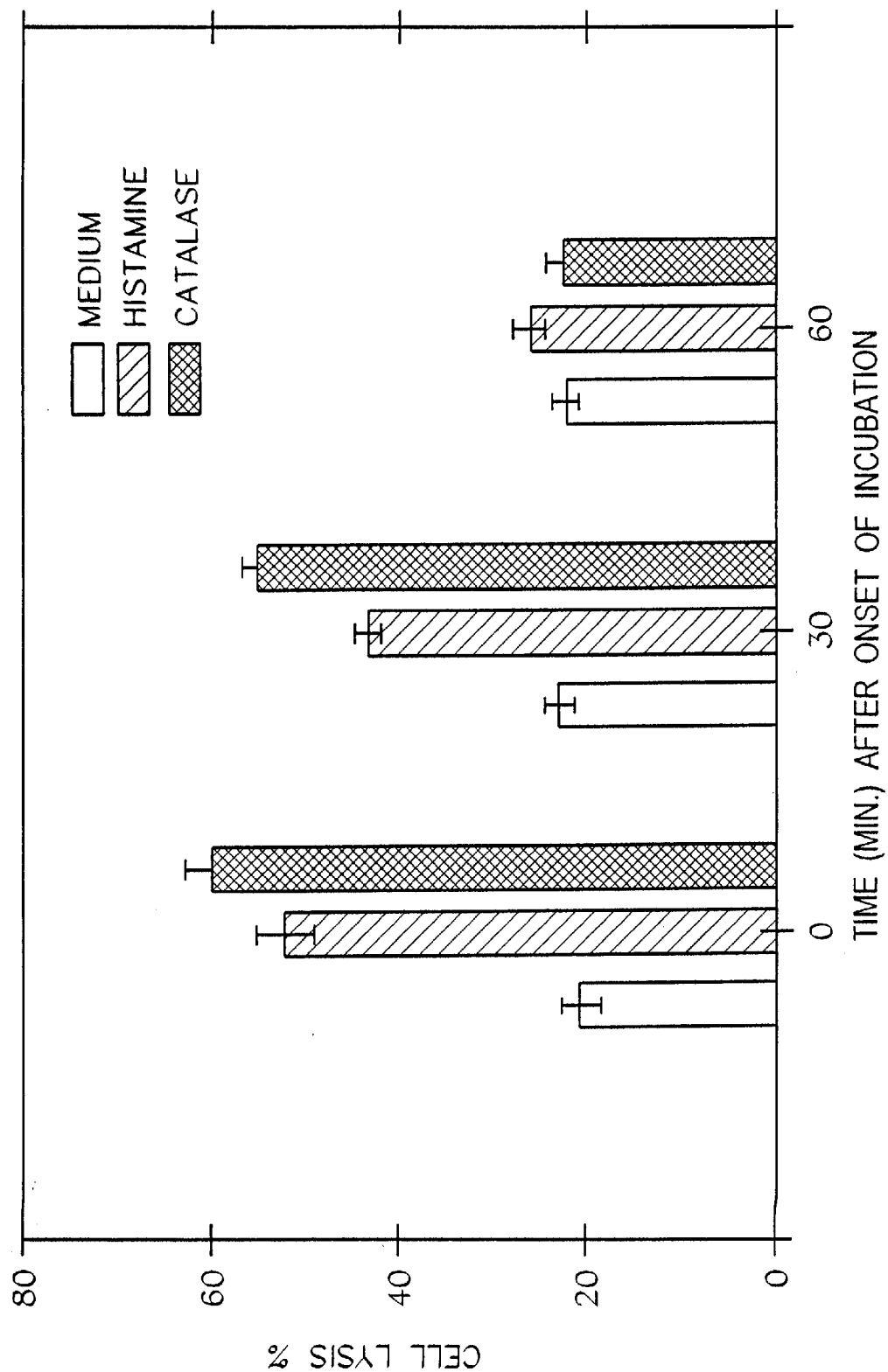
FIG. 5 illustrates the kinetics of monocyte-induced inhibition of NK cell cytotoxicity. A mixture of NK cells and monocytes were treated with culture medium (open bars), histamine (hatched bars) or catalase (filled bars) at the indicated time points after the start of the microtoxicity assay.

A mixture of enriched NK cells and monocytes were treated with culture medium (control), histamine ($10^{-4}$ M), or catalase (20 U/ml) and assayed for microcytotoxicity against target K562 cells as described above in connection with Example 1. It was found that catalase and histamine were effective in inhibiting the NK cell suppressive signal only when these compounds were added within the first hour of incubation of monocytes with NK cells. The results of this testing are shown in FIG. 5. The data shown is cell lysis %±s.e.m. of sextuplicates.

In additional experiments, NK cell enriched lymphocytes were pretreated in petri dishes with culture medium (control), catalase or histamine, in the concentrations indicated below in Table II, in the presence or absence of monocytes. After 1 hour incubation, nonadherent lymphocytes were recovered, washed twice, and assayed for cytotoxicity as described above. We wished to determine whether the NK cell inhibitory signal was reversible by removal of monocytes and removal of monocyte-derived products. It was found that lymphocytes recovered from monocyte/NK cell mixtures pretreated with catalase or histamine were more cytotoxic against K562 target cells than control mixtures pretreated with medium only. The results of this testing are shown below in Table II. Data are cell lysis %±s.e.m. of sextuplicates and are the results of 2 separate experiments.

TABLE II

Irreversible inhibition of NK-cells by monocytes and $H_2O_2$.

| exp. no. | pretreatment | conc. | MO | cell lysis %[a] |
|---|---|---|---|---|
| 1 | medium | | − | 66 ± 3 |
| | histamine | $10^{-5}$ M | − | 59 ± 3 |
| | catalase | 20 U/ml | − | 67 ± 2 |
| | medium | | + | 14 ± 1 |
| | histamine | $10^{-5}$ M | + | 51 ± 2 |
| | catalase | 20 U/ml | + | 48 ± 3 |
| 2 | medium | | − | 59 ± 3 |
| | $H_2O_2$ | 1.5 × $10^{-6}$ M | − | 26 ± 2 |
| | " | 3 × $10^{-6}$ M | − | 12 ± 1 |
| | " | 6 × $10^{-6}$ M | − | 2 ± 1 |

[a]NK-cell-enriched lymphocytes were pretreated in petri dishes with culture medium (control), histamine, or catalase at indicated final concentrations in the presence (MO+) or absence (MO−) of monocytes. Thereafter, nonadherent lymphocytes were recovered, washed twice and assayed for cytoxicity against K562 target cells. Data are cell lysis % ± s.e.m. of sextuplicates and show results from two separate experiments.

These data show that the inhibition of NK cells is evoked within the first hour of incubation with monocytes and that the inhibition is not reversible by removal of monocytes or monocyte derived factors. To confirm this finding, enriched NK cells were treated with $H_2O_2$ for 20 minutes followed by extensive washing and assay for cytotoxicity. Pretreatment with $H_2O_2$ at micromolar concentrations was sufficient to effectively inhibit NK cell cytotoxicity. The results of this testing are shown in Table II.

Histaminergic Regulation of the Respiratory Burst of Monocytes

Histamine has been reported to affect several functions ascribed to monocytes and macrophages, but effects of histamine on the respiratory burst of monocytes have remained unknown. To determine these effects, we first tested whether histamine could act as a scavenger of $H_2O_2$ or its radical metabolites in a cell free system. We then studied the effects of histamine and $H_2R$-interactive compounds on the respiratory burst activity of monocytes. These experiments are described in the following Examples.

EXAMPLE 13

Chemiluminescence (CL) of cells was recorded at 37° C. in a 6-channel Biolumat LB 9505 (Berthold Co., Wildbad, Germany) using 4 ml polypropylene tubes as described by Lock et al. *Anal. Biochem.* 173:450 (1988). The reaction mixture contained 0.8 ml elutriated monocytes ($5×10^6$ cells/ml). The tubes were allowed to equilibrate for 5 minutes at 37° C. before formylmethionyl-leucyl-phenylalanine (fMLP; Sigma; $10^{-7}$ M final concentration) and luminol (Sigma; $10^{-6}$ M) were added and light emission recorded. Formylmethionyl-leucyl-phenylalanine was dissolved to $10^{-2}$ M in dimethyl sulfoxide and subsequently diluted in Krebs-Ringer phosphate buffer supplemented with glucose (10 mM), $Ca^{2+}$ (1 mM), and $Mg^{2+}$ (1.5 mM). Luminol was dissolved in 0.1 mM NaOH to $5×10^{-2}$ M and further diluted in Krebs-Ringer phosphate buffer.

The CL recorded with $H_2O_2$ and/or MPO (10 μg/ml) or $H_2O_2$ and horseradish peroxidase (HRP; Calbiochem, La Jolla, Calif.) was unchanged by histamine ($10^{-4}$ M). Further, we used an assay system in which lysis of elutriated, $^{51}Cr$-labelled RBC was measured in microplates. Addition of $H_2O_2$ ($5×10^{-5}$ M) to $10^5$ RBC induced lysis of approximately 50% of RBC. Histamine ($10^{-4}$ M) did not alter the level of RBC killing induced by $H_2O_2$. It is therefore concluded that histamine is not a scavenger of $H_2O_2$ or its radical metabolites.

EXAMPLE 14

In a second set of experiments, effects of histamine and $H_2R$-interactive compounds on the respiratory burst activity, as measured by the luminol-enhanced CL response of enriched, elutriated monocytes, were studied. Monocytes were treated with culture medium (control), histamine ($10^{-5}$ M), sodium azide ($10^{-5}$ M), or histamine and sodium azide as described below. Emission of CL was recorded after addition of fMLP at time=0.

Figure 6A:
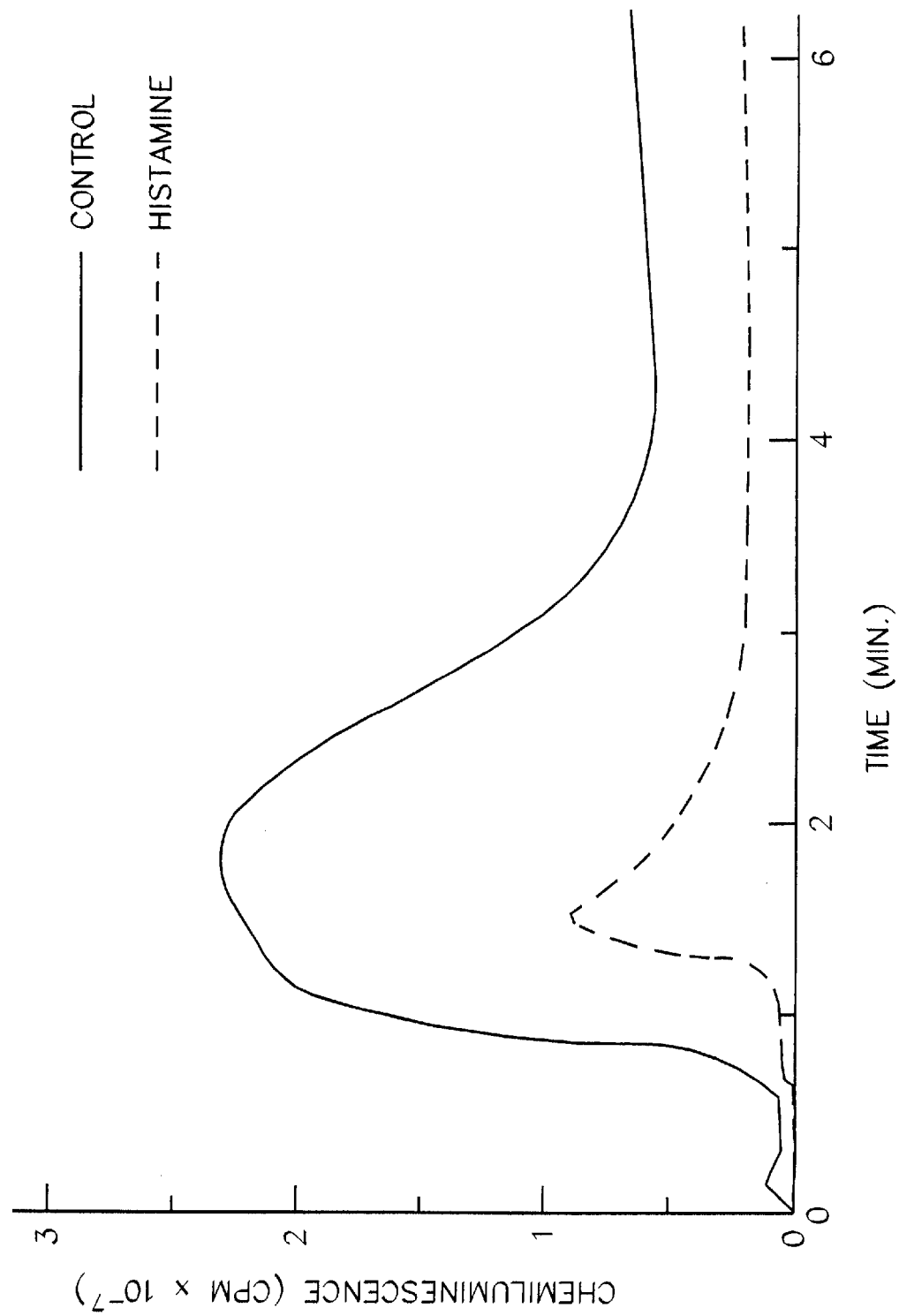
FIG. 6 shows that histamine inhibits the generation of hydrogen peroxide in monocytes. The luminol-enhanced chemiluminescence response of monocytes treated with culture medium (solid line) or histamine (dotted line) is shown in FIG. 6A.
FIG. 6B shows the response of monocytes treated with sodium azide (control, solid line), or histamine plus sodium azide (dotted line).

It was found that histamine effectively inhibited both the burst activity of unstimulated monocytes and the induction of burst by fMLP. The results of this are shown in FIG. 6A. The inhibitory effect of histamine was dose dependent at final histamine concentrations of $10^{-4}$–$10^{-7}$ M.

Figure 6B:
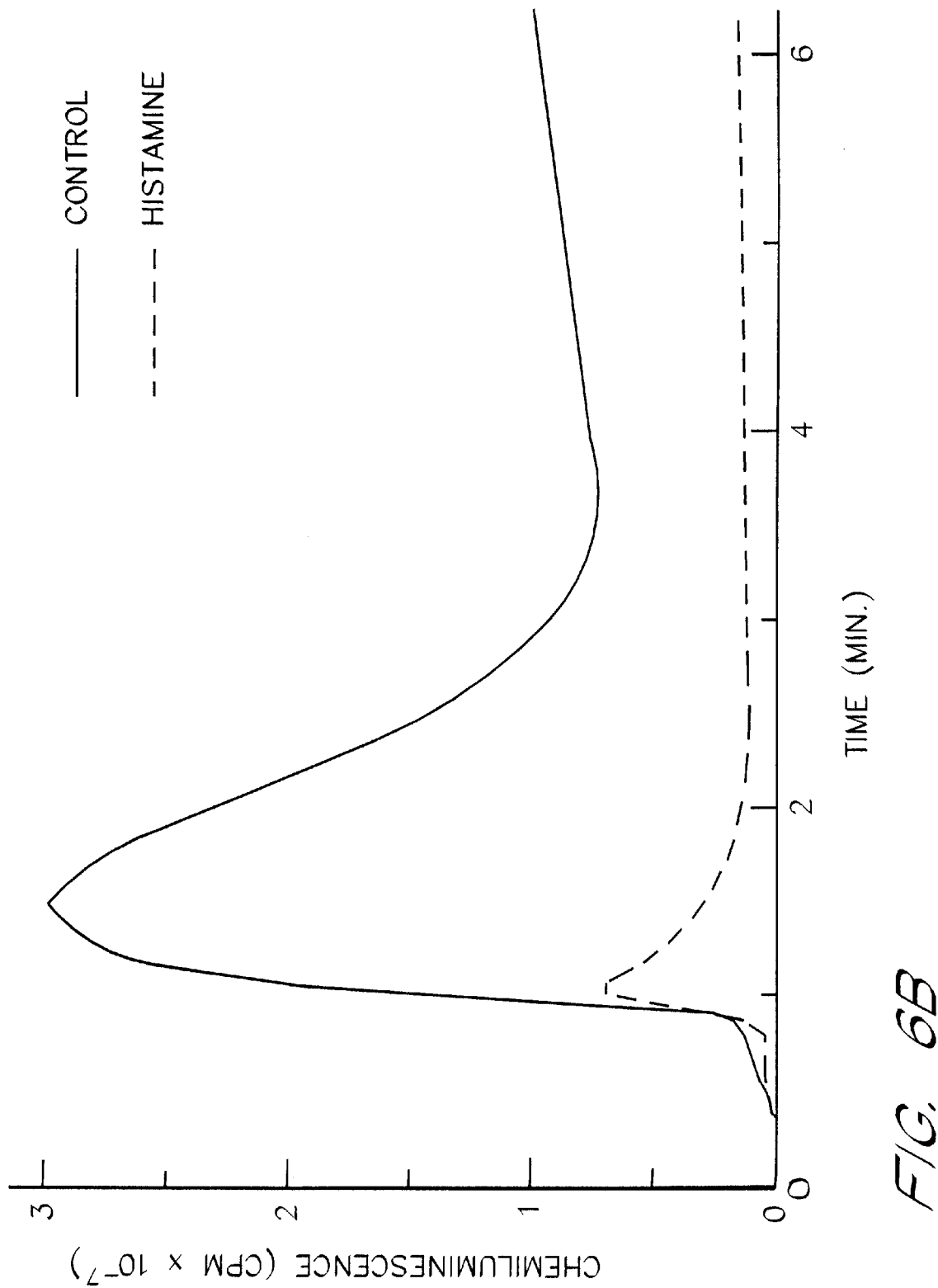

To assess whether histamine acted by inhibiting the generation of $H_2O_2$ or by reducing the availability of peroxidase, we next studied the effects of histamine in monocytes treated with sodium azide to inhibit endogenous myeloperoxidase (MPO) and with exogenous, azide-insensitive peroxidase (HRP) in excess. Histamine inhibited the fMLP induced CL response also in this type of assay, showing that histamine specifically inhibits the formation of $H_2O_2$ in monocytes. The results of this testing are shown in FIG. 6B.

Dimaprit, (SK&F, Hertfordshire, England), a specific $H_2R$ agonist, mimicked the effect of histamine on the respiratory burst of monocytes. In contrast, nor-dimaprit, (SK&F, Hertfordshire, England), an $H_2R$ inactive structural analog of dimaprit, was ineffective. A striking difference between histamine and dimaprit was that whereas histamine blocked respiratory burst activity within seconds, the effect of dimaprit was not maximal until after 10–15 minutes of incubation (data not shown).

Figure 7:
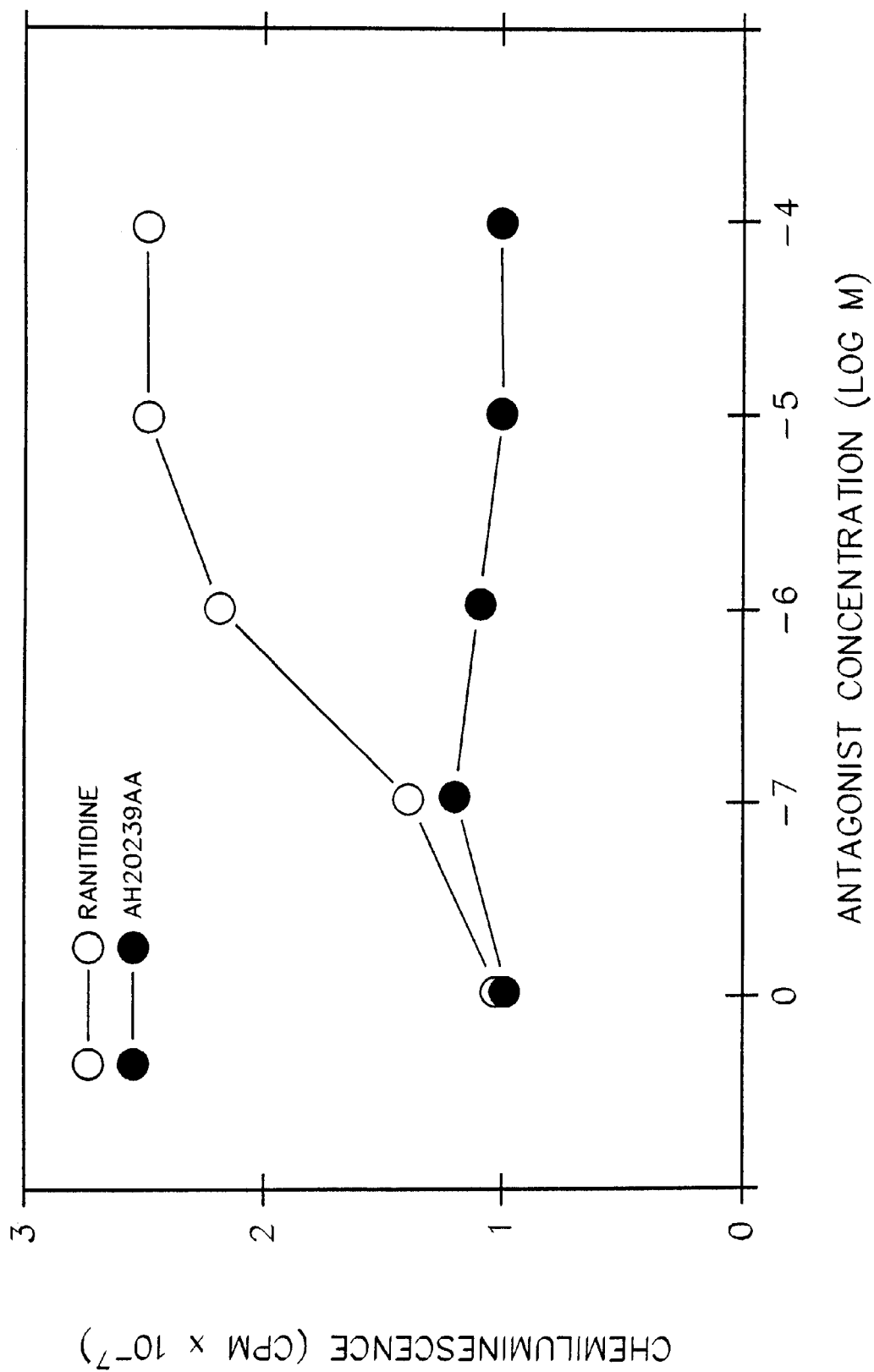
FIG. 7 shows that histamine $H_2$-type receptors transduce the effects of histamine on the respiratory burst of monocytes. Monocytes were treated with histamine plus ranitidine (open circles) or AH20239AA (filled circles).

FIG. 7 shows that the effects of histamine were entirely blocked by simultaneous treatment with the specific $H_2R$ antagonist ranitidine (Glaxo). To exclude non-specific effects of ranitidine, we used a ranitidine analog (AH20239AA; $C_{13}H_{22}O_4$; Glaxo) in which the thioether of ranitidine is replaced by an ether, thereby strongly reducing its $H_2R$ antagonist properties. In these experiments, monocytes were treated with histamine ($10^{-5}$ M) together with ranitidine or AH20239AA at final concentrations indicated in FIG. 7. All cells were treated with fMLP at time=0. Peak CL recorded in untreated monocytes (control) was $2.5 \times 10^7$ cpm.

The chemical control to ranitidine, AH20239AA, was more than 100-fold less potent than ranitidine in antagonizing the effects of histamine on the suppression of NK cell function by monocytes, as well as the inhibition of respiratory burst activity by histamine, as shown in FIG. 7. The effects of histamine on the respiratory burst activity of monocytes, therefore, are specifically transduced by $H_2R$.

CONCLUSION

We have discovered that hydrogen peroxide is a pivotal mediator of monocyte-derived, NK cell suppressive signal. The inhibitory effective of hydrogen peroxide on NK cells was not catalyzed by the addition of MPO, thus demonstrating that the MPO activity is not required to mediate NK cell inhibitory signals. Further, scavengers of MPO catalyzed radicals do not affect the inhibition of NK cell function induced by monocytes.

It is clear from our results that histamine, serotonin, or other $H_2$ receptor agonists, acting via monocyte $H_2$ receptors, inhibit the generation of reactive oxygen products by monocytes, and thereby inhibit the NK cell suppressive signal. It is clear that scavengers of hydrogen peroxide also act to inhibit the NK cell suppressive signal.

We have thus shown that treatment with a combination of an NK cell activating cytokine or other compound and a hydrogen peroxide scavenger or inhibiting compound in the presence of monocytes prevents the inactivation of NK cells and enhances NK cell cytotoxicity against tumor cells. These are unexpectedly superior results, since under similar circumstances, NK cell activators alone had no such beneficial effect. Of particular importance is that the potentiation of the anti-tumor effect of the NK cell activators induced by the concomitant treatment with a peroxide scavenger or inhibiting compound permits a reduction in the high doses of lymphokines which are used in cancer therapy. Advantageously, high dose treatments of lymphokines and the accompanying serious side effects can be eliminated by the method of the present invention.

What is claimed is:

1. A method for providing activated natural killer (NK) cells comprising the steps of:

administering to a population of cells which includes lymphocytes and monocytes, an effective amount of an NK cell activating cytokine, wherein said cytokine is selected from the group consisting of Interleukin-1 (IL-1), Interleukin-12 (IL-12) Interleukin-15 (IL-15), Interferon-β (IFN-β), and Interferon-γ (IFN-γ), or an NK cell activating flavonoid, wherein said NK cell activating flavonoid is selected from a group consisting of flavone-8-acetic acid (FAA) and xanthenone-4-acetic acid (XAA); and administering histamine, other $H_2$-receptor agonist or serotonin.

2. The method of claim 1, wherein said population of cells is located in vivo.

3. The method of claim 1, wherein the administration of said NK cell activating cytokine or said flavonoid and said histamine, other $H_2$-receptor agonist or serotonin is performed simultaneously.

4. The method of claim 1, wherein the administration of said histamine, other $H_2$-receptor agonist or serotonin is performed within 24 hours of the administration of said NK cell activating cytokine or flavonoid.

5. The method of claim 4, wherein said cytokine is administered in a dose of from about 1,000 to about 300,000 U/kg/day.

6. The method of claim 4, wherein said flavonoid is administered in a dose of from about 1 to about 100,000 mg/day.

7. The method of claim 2, wherein said histamine, other $H_2$-receptor agonist or serotonin is administered in a dose of from about 0.1 to about 10 mg/day.

8. A method for providing activated natural killer (NK) cells comprising the steps of:

administering to a population of cells which includes lymphocytes and monocytes, an effective amount of an NK cell activating cytokine, wherein said cytokine is selected from a group consisting of Interleukin-1 (IL-1), Interleukin-12 (IL-12), Interleukin-15 (IL-15), Interferon-β (IFN-β), and Interferon-γ (IFN-γ); or a NK cell activating flavonoid, wherein said flavonoid is selected from a group consisting of flavone-8-acetic acid (FAA) and xanthenone-4-acetic acid (XAA); and administering a hydrogen peroxide scavenger.

9. The method of claim 8, wherein said hydrogen peroxide scavenger catalyzes the decomposition of hydrogen peroxide.

10. The method of claim 9, wherein the compound is selected from the group consisting of catalase, glutathione peroxidase, and ascorbate peroxidase.

11. The method of claim 8, wherein said population of cells is located in vivo.

12. The method of claim 8, wherein the administration of said NK cell activating cytokine or said flavonoid and said hydrogen peroxide scavenger is performed simultaneously.

13. The method of claim 8, wherein the administration of said NK cell activating cytokine or said flavonoid and said hydrogen peroxide scavenger is performed within 24 hours.

14. The method of claim 11, wherein said cytokine is administered in a dose of from about 1,000 to about 300,000 U/kg/day.

15. The method of claim 11, wherein said flavonoid is administered in a dose of from about 1 to about 100,000 mg/day.

16. The method of claim 11, wherein said hydrogen peroxide scavenger is administered in a dose of from about 0.1 to about 10 mg/day.

* * * * *